United States Patent [19]

Chang

[11] Patent Number: 4,591,570

[45] Date of Patent: May 27, 1986

[54] MATRIX OF ANTIBODY-COATED SPOTS FOR DETERMINATION OF ANTIGENS

[75] Inventor: Tse-Wen Chang, Paoli, Pa.

[73] Assignee: Centocor, Inc., Malvern, Pa.

[21] Appl. No.: 463,188

[22] Filed: Feb. 2, 1983

[51] Int. Cl.[4] ............... G01N 33/543; G01N 33/552; G01N 33/545

[52] U.S. Cl. .................................... 436/518; 435/7; 435/300; 436/519; 436/531; 436/532; 436/527; 436/809; 436/815

[58] Field of Search .............. 435/7, 300; 436/519, 436/532, 531, 527, 809, 815, 518

[56] References Cited

U.S. PATENT DOCUMENTS

| | | | |
|---|---|---|---|
| 3,770,383 | 11/1973 | Price | 23/253 |
| 4,154,795 | 5/1979 | Thorne | 435/300 |
| 4,216,245 | 8/1980 | Johnson | 422/56 |
| 4,228,127 | 10/1980 | Acevedo et al. | 436/808 |
| 4,317,810 | 3/1982 | Halbert | 436/809 |
| 4,357,142 | 11/1982 | Schall | 436/809 |
| 4,468,371 | 8/1984 | Chen et al. | 422/102 |
| 4,471,056 | 9/1984 | Grumet et al. | 436/513 |

OTHER PUBLICATIONS

Engvall et al., J. Immunology, vol. 109 (No. 1) (Jul., 1972), pp. 129–135.

"Methods in Enzymology", Langone et al., eds., vol. 74, Immunochemical Techniques, Part C, pp. 90–105 by Sedlacek, H. H., et al., Academic Press Inc., New York, 1981.

"Chemical Abstracts", Michaelsen, et al., 97: 37269y (1982).

Chang, T., J. Immunol. Meth., vol. 65 (1983), pp. 217–223.

The Antigen Spot Test (AST): "A Highly Sensitive Assay for the Detection of Antibodies"; Herbrink, P. et al., J. Immunol. Meth. 48:293 (1982).

"A Dot-Immunobinding Assay for Monoclonal and Other Antibodies", Hawkes et al., Anal. Biochem. 119:142 (1982).

Primary Examiner—Christine M. Nucker
Assistant Examiner—Stephen C. Wieder
Attorney, Agent, or Firm—Hamilton, Brook, Smith & Reynolds

[57] ABSTRACT

This invention relates to a novel immunoassay device and method for the determination of antigenic substances. The device essentially comprises a pattern or array of minute antibody-coated spots on the surface of a support. The array of antibody-coated spots is preferably in the form of a rectangular matrix. Each antibody-coated spot is made up of antibodies of a different and distinct specificity. A large number of different antibody-coated spots can be assembled on a very small portion of the surface of the support. The spots serve as tiny, specific immunoadsorbents of cells. The expression of particular surface antigen by cells may be detected by determining to which antibody-coated spot the cells bind.

21 Claims, 7 Drawing Figures

○ ● ○ ● ○
● ○ ● ○ ●   ○ Anti-Lyt 2.1
○ ● ○ ● ○
● ○ ● ○ ●   ● Anti-Lyt 2.2
○ ● ○ ● ○
○ ● ○ ● ○
*Fig. 3A*
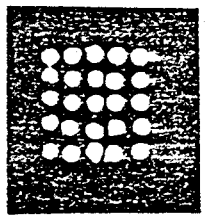
|IMM|
F1
*Fig. 3B*
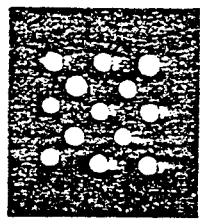
|IMM|
AKR
*Fig. 3C*
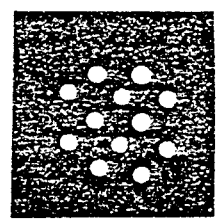
|IMM|
BALB/c
*Fig. 3D*

MATRIX OF ANTIBODY-COATED SPOTS FOR DETERMINATION OF ANTIGENS

DESCRIPTION

1. Technical Field

This invention is in the fields of cell biology and immunology, and particularly relates to a novel immunoassay device and method for the determination of antigenic substances.

2. Background

Antigens on the surface of cells can be detected by their specific reactivity with antibodies in a number of ways. The most commonly employed methods are immunofluorescence staining, radiobinding assays and complement-mediated cell lysis. In each method, the reactivity of cells with a particular antibody to a cell-surface antigen is determined separately, that is, the cells are incubated separately with each antibody to be tested. For example, in a complement-mediated cell lysis assay using microtiter plates, cells are incubated with antibody separately in each well of the microtiter plate. Usually, the microtiter plate is purchased with the desired antibodies frozen in the wells. After cells are added to each well and allowed to interact with antibody, complement is added along with a dye. Cells having antigens to which the antibodies bind are lysed and the lysed cells take up the stain. In this way cells to which antibodies have bound may be determined by visually inspecting the microtiter plate.

Frequently the number of individual tests in certain determinations can be very large. For instance, in tissue typing where the cell surface allo-antigens encoded by the gene loci of the histocompatibility complex are determined, at least 80 individual tests are required to determine the allotypes of the HLA-A, -B, -C and -DR transplantation antigens of a person. Such a large number of determinations entails a great deal of repetitive pipetting. Repetitive pipetting is undesirable because it is time consuming and because it increases the chance of error. Also a large number of determinations generally demand a large amount of sample and reagents which oftentimes are limited in supply because they are difficult or costly to obtain.

DISCLOSURE OF THE INVENTION

This invention exploits the phenomenon of immunoadherence to arrive at a simple yet powerful technique for the determination of specific antigenic substances on the surface of cells.

In its broadest sense this invention constitutes a novel immunoassay device and method for detecting antigenic substances. The invention is especially useful for determining the presence of particular antigens on the surface of cells, but is not limited to this use alone, as it may be employed for determining antigens in solution as well.

The device essentially comprises a pattern or array of minute antibody-coated spots on the surface of a support. Each antibody-coated spot is made up of antibodies of a different and distinct specificity. The spots serve as tiny, specific immuno-absorbents of cells. The expression of particular surface antigen by cells may be detected by determining to which antibody-coated spot the cells bind. A large number of different antibody-coated spots can be assembled on a very small portion of the surface of the support.

The invention represents a major simplification of existing immunocytological and immunochemical methodology in that it eliminates the need for repetitive pipetting when a large number of individual tests for different antigens are performed such as in tissue typing. Other significant advantages of the invention are that all tests with antibodies may be performed simultaneously in one location, only a single application of sample is required as opposed to the repetitious pipetting of sample into a large number of separate wells or tubes, and very small amounts of sample and reagents are consumed. Also this invention eliminates the need for costly reagents such as complement which is required, as its name implies, in the complement-mediated cytolysis technique.

BRIEF DESCRIPTION OF THE DRAWINGS

FIG. 1 shows the binding of mononuclear cells from an individual with allotype HLA-A2 to anti-HLA-A2 antibody spots on glass surface.

FIG. 3 shows the binding of thymocytes from AKR/H, BALB/c, and their F1 to antibody matrixes containing anti-Lyt 2.1 and anti-Lyt 2.2.

FIG. 3a shows schematically the arrangements of the two antibodies in the matrix. Coating of antibodies, application of cell samples, and photography were described in the Examples.

FIG. 3b is the cell binding result with thymocytes of (AKR/J×BALB/c)F1.

FIG. 3c is the cell binding result with thymocytes of AKR/J.

FIG. 3d is the cell binding result with thymocytes of BALB/c.

BEST MODE FOR CARRYING OUT THE INVENTION

Figure 1A:
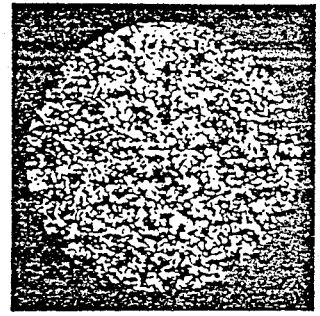
FIG. 1a shows the binding of the mononuclear cells to an anti-HLA-A2 antibody spot of 1 mm in diameter.

The immunoassay device of this invention comprises a support which has on its surface an array of antibody-coated areas or spots. Preferably, the support is a solid substance having a flat, planar surface such as a glass or plastic coverslip. The antibody-coated areas form small spots on the surface of the support surrounded by uncoated surface space. The antibodies in the antibody-coated spots are conjugated to the surface of the support; they may be either covalently or non-covalently bound thereto.

The most preferred arrangement of the spots on the surface of the support is a rectangular matrix. A matrix arrangement permits any spot to be readily identified by reference to coordinates giving the row and column number of the particular spot. The antibody spots should be closely spaced, thereby minimizing the surface space occupied by the complete arrangement of spots and in turn, minimizing the amount of sample needed. For instance, a 10 spot by 10 spot matrix should occupy about 1 cm$^2$ or less of the surface of the support.

In accordance with the invention, each spot, or each of certain sets of spots (such as the spots in one row or column), is made up of antibodies of single distinct specificity. Each spot, or each set of spots, contains antibodies whose specificity is different from the specificity of antibodies in the other spots. Thus in an 100 spot matrix 100 antibodies of different specificity may be tested. The antibody-coated spots serve as minute, specific immunoadsorbents for antigens with which the antibodies react. Antibody-coated spots made up of antibodies directed against a particular surface antigen of cells serve as specific immunoadsorbents for cells bearing that surface antigen.

The density of antibodies in the antibody-coated spots is related to the function of the spots as immunoadsorbents of cells. The density of coated antibodies, either covalently or non-covalently conjugated to the surface of the support, must be such that the cells bind tightly to the spots and remain bound during ordinary manipulation of the device in subsequent procedures for detecting cell binding. It is suspected that bridges between the surface antigens of the cells and the antibodies attached to the surface of the support must be numerous in order to achieve tight cell binding. Preferably, however, the density of antibodies should be sufficient to yield, upon contact with an appropriate concentration of cells which have surface antigens that bind to the antibodies, a microscopically uniform layer of bound cells covering the entire antibody-coated spot. The formation of such a uniform layer of cells is desirable because it facilitates detection of spots to which cells have attached. The density required to generate a microscopically uniform layer of cells is probably greater than the density minimally sufficient for tight cell binding.

The immunoassay device of this invention is produced by applying small volumes of antibody solutions to the surface of the support and allowing the solutions to remain on the support until the antibodies become absorbed to the surface. If desired, the antibodies may be chemically bound to the surface of the support by employing conventional methods for covalently binding proteins to a solid phase.

The solutions of antibodies may be applied to the surface in the form of tiny droplets. The volume of the droplet, of course, determines the size of the antibody-coated area. Preferably, the volume should range between 0.005–0.5 $\mu$l to yield antibody-coated dots with diameters of 0.25 mm–1.0 mm. The droplets should be placed on the surface so as to conform to the desired arrangement of antibody-coated spots.

The solution can be delivered by micropipet, or by other suitable means. Preferably the applicator should permit application of droplets to the support surface in precise positions to cover uniform areas of substantially the same size. Any means for applying the solutions other than in the form of droplets, as for example, a device that makes direct contact with the surface of the support to transfer the antibody solution thereto, should meet the same requirements.

The preferred concentration of antibodies in the solution applied to the surface for coating is about 10 $\mu$g/ml. It appears this is the optimal concentration for most antibodies. But because the binding of protein is dependent on its proportion in solution as well as its concentration, the solutions of antibodies must also be highly enriched in order to obtain a sufficiently dense antibody coat for the desired cell adherence. Monoclonal antibodies can be obtained in adequately enriched solutions for producing the antibody-coated spots. As more monoclonal antibodies against cell surface antigens become available, antibody matrixes for the determination of a wide range of antigens can be devised. Also polyclonal antibodies may be obtained in adequately enriched solutions for the purposes of this invention.

After the solutions of various antibodies have been applied to the surface of the support and allowed to remain on the surface for the time necessary for absorption or binding to occur, the entire surface of the support is flooded with a solution of protein or a solution of serum in order to dilute the unabsorbed antibodies and in order to block uncoated spaces and non-specific binding sites on the surrounding surface of the support. This protein solution is left on the surface for about 5–10 minutes. The device is then washed with distilled water and dried. The device may be used immediately, or it may be stored until use.

When the device is finished, antigen determinations can be performed in as little as 1–2 hours. Briefly, the method of using the device is as follows. Cells to be tested for the presence of certain surface antigens are placed in suspension in normal saline and applied to the surface of the device so that the cell entirely covers all the antibody-coated spots in the matrix. The number of cells needed to cover the entire matrix depends upon the size of the matrix and the type of cell. Generally, however, approximately $2 \times 10^6$ cells in a volume of 200 $\mu$l are sufficient to cover all antibody-spots in a 1 $cm^2$ matrix of spots.

After the suspension of cells is applied to the surface of the support as above, the cells are allowed to settle to the surface and react with the antibodies in the spots. Next, non-adherent cells are removed from the surface. This can be accomplished by washing and agitating the device or by any other suitable method which does not disrupt the adhered cells. The matrix of antibody spots is examined to determine to which spots cells have bound. Cells may be fixed and stained to aid in identifying the spots to which they have adhered.

The immunoassay device of this invention can be used not only to determine the presence of a specific antigen on the surface cells, but also to analyze functionally different cell subpopulations that express distinct differentiation antigens. It has been established that an antibody-coated solid surface can adsorb quantitatively from a mixed population of cells the cells that bear the specific surface antigen with which the antibody react. The antibody matrix method of this invention could be used to determine the proportion of specific subsets in a mixed population, for example, the proportion of B cells, T cells, and monocytes in the mononuclear cell population or the proportion of inducer and suppressor T cells in the T cell population. Since the murine monoclonal antibodies that react specifically with all these cells are available, an immunoadherence device and method to accomplish the aforementioned may be developed. Although these tests can now be done with fluorescence flow cytometry where each individual antibody analyzed separately, the antibody matrix method allows multiple determinations to be performed simultaneously.

Also, this invention is not limited to the detection of antigens on the surface of cells. It is also applicable to the determination of soluble antigens, viruses, or bacteria. Some potential uses include the determination of the isotypes, allotypes or idiotypes of an antibody and the typing of a viral or a bacterial sample.

The following examples are intended to illustrate more fully the invention.

EXAMPLES

Monoclonal antibodies

Mouse anti-human HLA-A2 (IgG1), which was originally developed by Parham and Bodner, Nature 276:397 (1978), was purchased from Atlantic Antibodies, Scarborough, ME. The specific antibody had been enriched by the supplier from ascites fluid by a series of salt fractionation procedures. Allogeneic mouse anti-Lyt 2.1 (IgG$_{2a}$) was originally developed by Shen and obtained from New England Nuclear, Boston MA in ascites fluid form. The IgG$_{2a}$ was enriched by absorbing it to protein A-Sepharose 4B column. Mouse anti-Lyt 2.2 (IgM) enriched from ascites fluid was a gift from Dr. David Raulet of the University of Pennsylvania. The original hybridoma was developed by Gottlieb et al., Immunogenetics 10:545 (1980).

Chemicals and specific glassware

Fluorescein isothiocyanate was purchased from Research Organics, Cleveland, Ohio. Pyrex disposable micro-sampling pipets (1–5 microliters) were from Corning Glass Works, Corning, NY. The pipets were heated and drawn into thinner pipets to deliver 0.005–1 ul. Graduations of 0.5 ul were marked by a fine-tip marker pen. Micro cover glasses (0.13–0.19 mm thick, 11×22 mm, 22×30 mm, and 22×40 mm) were obtained from Arthur H. Thomas Co. (catalog numbers 6663-F10, 663-K19, and 6663-K46).

Mice and cells

BALB/c mice were obtained from Charles River Breeding Laboratories, Wilmington, MA. AKR/J and (AKR/J×BALB/cJ) F1 mice were obtained from Jackson Laboratories, Bar Harbor, ME. These mice were 6–8 weeks old when used. Thymocytes were prepared by testing thymus through stainless screen. Human peripheral blood mononuclear cells were prepared by centrifuging heparinized blood on Ficoll/diatrizoate sodium solution (d=1.077) (Pharmacia, Piscataway, NJ). Mononuclear cells were recovered from the interface of the 2-layer discontinuous density gradient.

Coating of antibodies on cover glass slips

A small piece of section paper (10 divisions in ⅛ inch length) was taped underneath the cover slip. The cover slips were placed at the center of a 10 cm diameter petri dish. The surrounding space in the dish and the inside of the lid were covered with wet paper tissue to retain moisture. Unless specified otherwise, about 0.05 μl antibody solution was applied as a dot on the grid with a fine-tip 5 μl micropipet. Antibodies were diluted to 10 μg/ml with phosphate buffered saline, pH 7.4. Proper lighting was helpful for delivering droplets of uniform sizes. Application of droplets should be done in cold (4° C.) room, if the air in the laboratory is dry. After incubation at room temperature for 60 min or at 4° C. overnight, the paper tissue in the dish was removed and the cover slips were flooded swiftly with 30% calf serum to dilute the antibodies and to block uncoated space and binding sites. After 5–10 min, the cover slips were washed with distilled water and dried with an aspirator. The cover slips were immediately placed in petri dishes with the inside of the lids covered with wet paper tissue and the side of the dishes was sealed with parafilm. The slips were then stored at 4° C. until use.

Adhesion of cells to the antibody-coated glass slips

The antibody-coated slips were taped on petri dishes. Mouse thymocytes or human peripheral blood mononuclear cells were suspended at 1×10$^7$/ml in medium containing 1% fetal calf serum. A minimal suspension was placed on the antibody matrixes: about 50 μl for a 5×5 matrix and 200 μl for a 10×10 matrix. The cells were allowed to settle for 30 minutes at room temperature. About 10 ml phosphate buffered saline was added to the petri dish. Nonadherent cells were knocked off and flushed away by tapping the side of the dish 10–20 times. The retained cells on cover slips were then fixed by incubating in 10 ml formaldehyde solution (3.7%) for 30 min at room temperature. The cover slips were then washed with distilled water and air dried on paper tissue. In some cases, cells were further stained with fluorescein isothiocyanate (0.05 mg/ml in phosphate buffered saline) for 20 min at 37° C. before washing with distilled water and drying.

Evaluation of cell binding

All the binding could be evaluated simply by the naked eye (without the use of the microscope). Certain samples were photographed on a black, smooth-surface, non fractile paper with 5 or 30 times magnification using a stereomicroscope.

Binding of cells to small areas of antibody-coated surface

Various amounts of mouse anti-human HLA-A2 antibody (10 μg/ml), ranging from approximately 0.005–0.5 ul, were applied to small (11×22 mm) glass cover slips. Amounts larger than 0.05 μl could be measured and delivered. The amount of solution in droplets smaller than 0.05 μl was estimated by the number of droplets per unit volume delivered. For example, if 20 droplets resulted from the delivery of 0.1 μl, the average size of the droplets was 0.005 μl. After the cover slips were prepared as described above, peripheral blood mononuclear cells isolated from individuals with allotype A2 were applied to the antibody coated areas. After binding, nonadherent cells were washed away; adherent cells were fixed with formaldehyde and dried. Cover slips were examined with a regular microscope and photographed with a stereomicroscope.

Figure 1B:
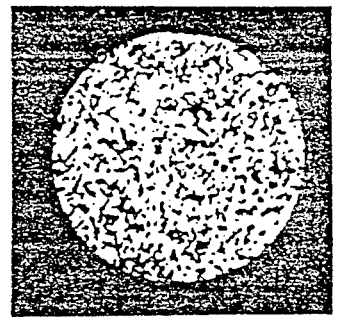
FIG. 1b shows binding to a spot of 0.5 mm in diameter.
Figure 1C:
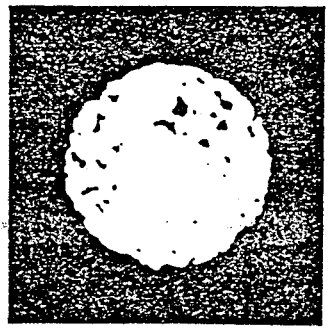
FIG. 1c shows binding to a spot of 0.25 mm in diameter.

FIG. 1 shows the 1 mm, 0.5 mm, and 0.25 mm diameter dots at 50 times magnification. The glass surface is microscopically uniform.

Table 1 summarizes the cell-adsorbing capacity of antibody dots of varying sizes. The cover slips were placed on a heamacytometer and total number of cells were estimated from the number of cells in a unit area and the diameter of the dots. The numbers probably represent the maximal capacity, since almost all space in the dots is filled. The smallest 0.25 mm dots are still easily visible and can contain 1100 cells. These numbers should be within the limits that can be quantitated somehow with automatic analytical instruments.

TABLE 1

| Number of cells in antibody dots of various sizes | | | |
|---|---|---|---|
| Size of dots (diameter) | 1 mm | 0.5 mm | 0.25 mm |
| Number of cells[a] | 17000 ± 2000 | 4500 ± 300 | 1100 ± 200 |

[a]Numbers are mean ± standard deviation of three determinations.

Analytical capacity of antibody matrixes

Figure 2:
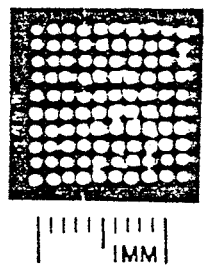
FIG. 2 shows the binding of mononuclear cells to a 10×10 spot matrix of anti-HLA-A2 antibody-coated spots.

If antibodies of relevant but distinct specificities can be prepared and purified, they can be coated on a small area on a solid phase and used to analyze antigens. The most convenient organization of such antibody dots would appear to be arrays as exemplified in FIG. 2, in which one hundred antibody dots were arranged in a 10×10 "matrix" square. In this example, mouse anti-human HLA-A2 was the antibody, and peripheral blood mononuclear cells from an individual with A2 allotype was the cell antigen.

Table 2 elucidates the analytical capacity of antibody matrixes. The discussion was based on a matrix area of 1 cm$^2$. Assuming all antibodies are available, the typing for the HLA-A, B, C, and DR, which have about 80 allotypes altogether, can be performed with one cell sample application. With the 0.25 mm dots, the tests of each individual allotypes can be repeated five times. It is apparent that the analysis of the cell binding results would be facilitated with proper instruments. Table 2 also indicates that each individual antibody matrix may have the capacity equivalent to one or several microtiter plates.

TABLE 2

The analytical capacity of using antibody matrixes of 1 cm$^2$ to determine antigens.

| Size of dots (diameter) | 1 mm | 0.5 mm | 0.25 mm |
|---|---|---|---|
| Number of total dots[a] | 25 | 100 | 400 |
| Number equivalent of microtiter plates (60 wells) | 0.5 | 1.5 | 7 |
| Number of replicates for HLA typing (80 total allotypes) | — | 1 | 5 |

Cell sample and antibody requirement using antibody matrix analysis

Assuming mononuclear cells are 7 μm in diameter (some are obviously larger), a square of 1 cm$^2$ may be completely covered with 1.5×10$^6$ cells. In fact, in the present studies 5×10$^5$ cells (in 50 μl) and 2×10$^6$ cells (in 100 μl) were applied on areas of 0.25 cm$^2$ (5×5 matrix) and 1 cm$^2$ (10×10 matrix), respectively. Since one ml of blood contains on the average 1×10$^6$ mononuclear cells, a few ml of blood is enough for a 1 cm$^2$ antibody matrix test.

The antibody matrix requires only very small amounts of reagents. If an antibody is coated at 10 μg/ml concentration, which is optimal for most antibodies, 1 mg antibody can make 200,000 antibody dots of 0.5 mm diameter (see Table 3).

TABLE 3

Antibody solution required to coat antibody dots.

| Size of dots (diameter) | 1 mm | 0.5 mm | 0.25 mm |
|---|---|---|---|
| Approximate volume antibody solution | 0.5 μl | 0.05 μl | 0.005 μl |
| Number of dots that 1 mg antibody can coat[a] | 20,000 | 200,000 | 2,000,000 |

[a]Antibody concentration is 10 μg/ml.

Binding of cells to specific antibody in the antibody matrix

Because the binding of a protein to a solid surface is dependent on not only its concentration but also its proportion in the solution, a specific antibody has to be rather enriched to be coated successfully. There are not many such antibodies available yet; the present studies use the antibodies that react with the allotypes of mouse T cell surface differentiation antigen Lyt-2 to examine the specificity of cell binding to antibody dots in antibody matrix. Anti-Lyt 2.1 and Lyt 2.2 monoclonal antibodies have been developed, and isotypes of the antibodies can be readily isolated from ascites of mice bearing the specific antibodyproducing hybridomas.

FIG. 3a shows schematically how the two antibodies are coated alternately to form 5×5 matrixes. The size of the matrixes are (0.5 cm)$^2$ and the size of the dots is 0.5 mm in diameter. Thymocytes from AKR (Lyt 2.1+), BALB/c (Lyt 2.2+), and (AKR×BALB/c) F1 (Lyt 2.1+ and 2.2+) were applied on the matrixes on a cover slip. FIGS. 3b, 3c, and 3d show that AKR cells bind to only anti-Lyt 2.1 spots, BALB/c cells bind to only anti-Lyt 2.2 spots, and cells of their F1 bind to both spots. The binding is very specific. In a single cell binding assay using 5×5 matrix as shown in FIG. 3, the test with anti-Lyt 2.1 was repeated thirteen times and the test with anti-Lyt 2.2 twelve times.

Industrial Applicability

It is contemplated that this invention will be employed in clinical and research laboratories in tests or procedures requiring multiple antigen determinations. Generally, preparation of the immunoassay device, a procedure which requires the coating of a large number of antibodies onto glass coverslips or other types of supports, is not for routine practice in these laboratories. In order for this invention to be widely used, the devices should be made commercially available to users. To manufacture the devices in large number, a mechanical applicator could be developed to apply the antibodies. As set forth above, the applicator should be able to precisely position the antibody-coated spots; also the applicator should be able to form spots of uniform shape (preferably round) and of substantially the same size.

For analysis of the results of cell binding to the antibody-coated spots, an automatic analyzer that would read cell binder to each antibody-coated spot and process this data is highly desirable.

Equivalents

Those skilled in the art will recognize, or be able to ascertain, using no more than routine experimentation, many equivalents to the specific embodiments of the invention described herein. Such equivalents are intended to be encompassed by the following claims.

I claim:

1. An immunoassay device comprising a support having a substantially planar surface and having an array of small, discrete, closely spaced antibody-coated areas on the planar surface, the antibodies in the discrete, antibody-coated surface areas being absorbed to the planar surface at a density and uniformity such that when cells bearing a surface antigen are brought into contact in sufficient concentration with a discrete, antibody-coated area containing antibodies which bind the antigen, the cells adhere tightly to the discrete, antibody-coated area and form a layer of bound cells which is substantially microscopically uniform over essentially all of the discrete antibody-coated area.

2. An immunoassay device according to claim 1, wherein all of the discrete, antibody-coated areas have substantially the same size and shape.

3. An immunoassay device according to claim 1, wherein the antibodies in the discrete, antibody-coated areas are covalently bound to the surface of said support.

4. An immunoassay device according to claim 1, wherein the antibody in each of the discrete, antibody-coated surface areas, or in identifiable sets of said antibody-coated surface areas, is antibody of different and distinct specificity.

5. An immunoassay device according to claim 1, wherein the antibodies in the discrete, antibody-coated areas are monoclonal antibodies.

6. An immunoassay device according to claim 1, wherein the antibodies in the discrete, antibody-coated areas are monoclonal antibodies.

7. An immunoassay device according to claim 1, wherein the support is a glass or plastic coverslip.

8. An immunoassay device according to claim 1, wherein the array of discrete, antibody-coated areas is a rectangular matrix.

9. An immunoassay device according to claim 1, wherein discrete, antibody-coated surface areas are dots having diameters of about 0.25 mm to 1.0 mm.

10. An immunoassay device according to claim 1, wherein said antibody-coated dots on the surface of the support are arranged in a compact 5–20 dot by 5–20 dot rectangular matrix.

11. An immunoassay device according to claim 9, wherein the entire rectangular matrix is contained within an area of about 0.5–1.0 cm$^2$ of the surface of the support.

12. A method of producing an immunoassay device which comprises the steps of:
(a) applying droplets of substantially enriched aqueous solutions of antibodies of distinct specifications to a substantially planar surface of a support, locating said droplets so that they cover small, discrete, closely spaced areas of the planar surface of the support and form an array;
(b) allowing said aqueous solutions of antibodies to remain on said areas of the surface for a period of time long enough for the antibodies in solution to be adsorbed to said areas of the surface to form discrete, antibody-coated areas;
(c) swiftly flooding the entire surface of the solid support with an aqueous solution of protein in order to dilute the unadsorbed antibodies in the various solutions of antibodies and in order to block non-specific binding sites in areas of the surface of the solid support which surround the antibody-coated areas; and
(d) washing and drying the device.

13. A method according to claim 12, wherein in step a the concentration of antibodies in said aqueous solutions of antibodies is about 10 μg/ml.

14. A method according to claim 12, wherein in step a each solution of antibodies is applied to the surface of the solid support in the form of a tiny droplet having a volume of about 0.005 μl–0.5 μl.

15. A method according to claim 12, wherein said small, discrete areas of the surface of the support to which said solutions of antibodies are applied are dots having diameters of about 0.25 mm to 1.0 mm.

16. A method according to claim 12, wherein said dots are located on the surface of the solid support to form a rectangular matrix.

17. A method of determining the presence of particular antigens on the surface of cells, comprising the steps of:
(a) applying a suspension of cells to a substantially planar surface of a support, said support having upon the planar surface an array of small, discrete, antibody-coated spots, each spot, or each of certain sets of spots, coated with antibodies of different and distinct specificity, the antibodies in the discrete, antibody-coated spots being adsorbed to the surface at a density and uniformity such that when cells bearing a surface antigen are brought into contact in sufficient concentration with a discrete, antibody-coated spot containing antibodies which bind the antigen, the cells adhere tightly to the discrete, antibody-coated spot and form a layer of bound cells which is substantially microscopically uniform over essentially all of the discrete, antibody-coated spot;
(b) allowing the cells to settle upon the surface of the support so that the cells come into contact with all of the discrete antibody-coated spots;
(c) allowing the cells to react with the antibodies in the discrete antibody-coated spots;
(d) removing non-adherent cells;
(e) determining to which discrete antibody-coated spots the cells have adhered.

18. A method of determining the presence of particular antigens in a liquid comprising the steps of:
(a) applying a sample of the liquid containing antigens to a substantially planar surface of a support, said support having upon its planar surface an array of small, discrete antibody-coated spots, each spot coated with antibodies of different and distinct specificity, so that the antigen containing liquid comes into contact with all of the discrete, antibody-coated spots;
(b) allowing the antigens to react with the antibodies in the discrete, antibody-coated spots;
(c) washing the device to remove all unbound antigens;
(d) determining to which discrete, antibody-coated spots antigens are bound.

19. A method of determining the proportion of cells bearing specific surface differentiation antigens in a mixed population of cells comprising:
(a) applying a suspension of cells to a substantially planar surface of a support, said support having upon its planar surface an array of small, discrete, antibody-coated spots, each spot coated with antibody of different and distinct specificity for cell surface differentiation antigens, the antibodies in the discrete, antibody-coated spots being adsorbed to the surface at a density and uniformity such that when cells bearing a surface antigen are brought into contact in sufficient concentration with a discrete, antibody-coated spot containing antibodies which bind the antigen, the cells adhere tightly to the antibody-coated spot and form a layer of bound cells which is substantially microscopically uniform over essentially all of the discrete, antibody-coated spot;

(b) allowing the cells to settle upon the surface of the support so that the cells come into contact with all of the discrete, antibody-coated spots;
(c) allowing the cells to react with the antibodies in the discrete, antibody-coated spots;
(d) removing non-adherent cells;
(e) quantitating cells bound to the discrete, antibody-coated spots; and
(f) calculating the relative proportion of cells.

20. An immunoassay device according to claim 1, for tissue typing, wherein the antibody in each of the discrete, antibody-coated areas, or in identifiable sets of the antibody-coated areas, is specific for a different and distinct transplantation antigen.

21. An immunoassay device for tissue typing comprising a solid support having a substantially planar surface and an array of small, discrete, closely-spaced anti-HLA antibody-coated spots on the planar surface, the anti-HLA antibody in the discrete, antibody-coated surface area being adsorbed to the planar surface at a density and uniformity such that when cells bearing a surface antigen are brought into contact in sufficient concentration with a discrete, antibody-coated area containing antibodies which bind the antigen, the cells adhere tightly to the discrete, antibody-coated area and form a layer of bound cells which is substantially microscopically uniform over essentially all of the discrete antibody-coated area.

* * * * *